United States Patent [19]

Bowman

[11] 3,988,448
[45] Oct. 26, 1976

[54] 1,4-OXAZEPINES AS ANTIDEPRESSANT AGENTS
[75] Inventor: Robert Mathews Bowman, Summit, N.J.
[73] Assignee: Ciba-Geigy Corporation, Ardsley, N.Y.
[22] Filed: Nov. 25, 1974
[21] Appl. No.: 526,758

[52] U.S. Cl. .................................. 424/244; 260/333
[51] Int. Cl.² ........................................ A61K 31/33
[58] Field of Search ..................... 424/244; 260/333

[56] References Cited
UNITED STATES PATENTS
3,391,149   7/1968   Easton et al. ..................... 260/294.8

Primary Examiner—James O. Thomas, Jr.
Assistant Examiner—Allen J. Robinson
Attorney, Agent, or Firm—Joseph G. Kolodny; Theodore O. Groeger; John J. Maitner

[57] ABSTRACT

7,7-Diphenyl-hexahydro-1,4-oxazepines, e.g. those of the formula:

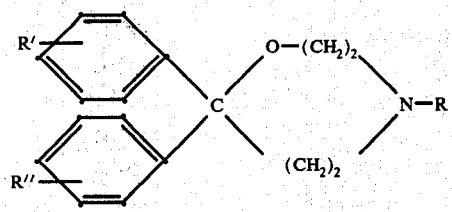

R = H, aliphatic, cycloaliphatic, araliphatic or aromatic radical
R′, R″ = H, alkyl, OH, alkoxy, alkyl-mercapto, halogen or $CF_3$ acyl derivatives, N-oxides and salts thereof are antidepressants.

4 Claims, No Drawings

1

1,4-OXAZEPINES AS ANTIDEPRESSANT AGENTS

SUMMARY OF THE INVENTION

The present invention concerns and has for its object the provision of new 7,7-diphenyl-hexahydro-1,4-oxazepines, more particularly of those corresponding to Formula I

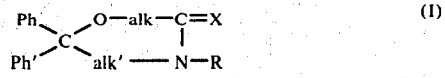

wherein X represents two hydrogen atoms or oxo, alk is lower alkylidene, alk' is lower alkylene separating the adjacent atoms by 2 carbon atoms, R is hydrogen, lower alkyl, alkenyl, alkynyl, (cycloalkyl, cycloalkenyl, Ph or Hc)-$C_mH_{2(m-q)}$, (PhCO, cyano, carboxy or carbalkoxy)-$C_nH_{2n}$, (hydroxy, halogeno, amino, mono-or dialkylamino)-$C_pH_{2p}$ or halogeno-$C_pH_{2p-2}$, each of Ph and Ph' is phenyl, unsubstituted or substituted by up to three members of lower alkyl, alkoxy, alkylmercapto, hydroxy, halogeno or trifluoromethyl, Hc is furyl, thienyl or pyridyl, unsubstituted or substituted by up to three lower alkyls, m is an integer from 0 to 4, n such from 1 to 4, p such from 2 to 4, q such from 0 to 2 and (m-q) is positive; or an acyl derivative of said compounds containing hydrogen bound to oxygen or nitrogen and being derived from an aliphatic or cycloaliphatic monocarboxylic acid, the N-oxide of said tertiary nitrogen compounds or a therapeutically acceptable acid addition salt thereof; of corresponding pharmaceutical compositions and of methods for the preparation and application of these products, which are useful antidepressant agents.

DESCRIPTION OF THE PREFERRED EMBODIMENTS

A lower alkylidene group alk is preferably methylidene, e.g. for the compounds I mentioned below, but also ethylidene or propylidene, and the lower alkylene group alk' is preferably ethylene, e.g. for the compounds listed on page 5, but also, for example, 1,2-propylene or-butylene.

A lower alkyl, alkenyl or alkynyl group R is preferably methyl, ethyl, n- or i-propyl or -butyl; allyl, methallyl, 2- or 3-butenyl or 3-methyl-2-butenyl; propargyl, 2- or 3-butynyl. A lower cycloalkyl or cycloalkenyl group is 3 to 7 ring-membered or 5 to 7 ring-membered respectively, such as cyclopropyl, cyclobutyl, cyclopentyl or cyclohexyl; 1-, 2- or 3-cyclopentyl or -cyclohexenyl.

Of the radicals Ph and Ph' one is preferably phenyl and the other phenyl, (lower alkyl)-phenyl, mono-, di- or tri-(lower alkoxy)-phenyl, (lower alkylmercapto, hydroxy, halogeno or trifluoromethyl)-phenyl, wherein alkyl has been illustrated above and preferably represents methyl, lower alkoxy or alkylmercapto are preferably methoxy or methylmercapto, but also ethoxy, n- or i-propoxy or -butoxy or ethylmercapto respectively, and halogeno is preferably fluoro, chloro or bromo. A carbalkoxy group is preferably carbomethoxy or carbethoxy and a mono-or dialkylamino group is preferably mono- or dimethyl- or-ethylamino, i-propylamino or di-n-propylamino. The heterocyclic radicals Hc are preferably unsubstituted, or substituted by up to three methyl groups, and advantageously attached to the oxazine ring via a methylene group ($m = 1, q = 0$).

The moeity $C_mH_{2(m-q)}$ is either a direct bond ($m=0$), or it preferably represents methylene or ethylene; 1-propenylene or 1-propynylene respectively ($m = 3, q = 1$ or 2); $C_nH_{2n}$ and $C_pH_{2p}$ preferably represent $(CH_2)_n$ and $(CH_2)_p$ respectively and halogeno-$C_pH_{2p-2}$ is preferably 3-halogenoallyl. Of said integers m is mainly 0 to 2 if q is 0, or 3 if q is 1 or 2, n is mainly 1 to 3, and p is mainly 2 or 3.

The acyl derivatives are preferably derived from the primary or secondary amines of Formula I (R = H or amino-$C_pH_{2p}$) and lower alkane, di-loweralkylamino-lower alkane or 3 to 7 ring-membered cycloalkane or cycloalkylalkane monocarboxylic acids, thus being open chain amides. Suitable acids for said derivatives are, for example, acetic, propionic, n- or i-butyric, α- or β-(dimethylamino, diethylamino, cyclopropyl, cyclopentyl or cyclohexyl)-acetic or -propionic acid; cyclopentane- or cyclohexane-or adamantanecarboxylic acid.

The N-oxides are preferably the 4-N-oxides of Formula I, wherein R is lower alkyl, (cycloalkyl or Ph)-$C_mH_{2m}$ or (PhCO or carbalkoxy)-$C_nH_{2n}$, and the acid addition salts are preferably derived from the therapeutically acceptable acids listed below.

The compounds of the invention exhibit valuable pharmacological properties, for example, imipramine-type antidepressant effects. This can be demonstrated in animal tests, using advantageously mammals, such as mice, rats or monkeys, as test objects. The compounds of the invention can be applied to the animals enterally, e.g. orally, or parenterally, e.g. subcutaneously, intraperitoneally or intravenously, for example in the form of aqueous solutions or starchy suspensions. The dosage may range between about 0.1 to 100 mg/kg/day, preferably between about 1 and 75 mg/kg/day, especially between about 10 and 50 mg/kg/day, An antidepressant effect is observed, for in the classical mouse tetrabenazine or rat reserpine ptosis tests, or preferably in the amphetamine interaction test (P. Carlton, Psychopharmacologie 1961 Vol. II, p. 364) performed psychopharmacologia male albino rats, which are trained to press a bar every 30 seconds, in order to avoid an electric shock applied through the floor grid. In case the animals receive 0.25 mg/kg/day or amphetamine i.p., their performing rate for avoiding said shocks during a test period of about 4–5 hours is slightly higher than that of placebo (saline) treated animals. In case the animals receive the compounds of the invention (or imipramine for control purposes) in the above-mentioned doses, preferably at 20 mg/kg/day i.p. and about 45 minutes later the amphetamine, their rate of avoiding the shocks is highest, as compared with that of rats receiving (a) saline alone, (b) saline and amphetamine, or (c) the compounds of the invention and saline. The results of said tests indicate that the compounds of the invention are highly active antidepressants with a rapid onset of action and, for this purpose, also well tolerated by the intravenous route of administration. Thus, for example, administration of the 4-allyl-7,7-diphenyl-hexahydro-1,4-oxazepine, a characteristic compound of the invention, when applied intravenously as a solution of its hydrochloride in physiologic saline to dogs at an infusion rate of about 0.5 mg/kg/min. × 180 is well tolerated by the animals, especially in view of their cardiac function. Accordingly, the compounds of the invention are useful antidepressants in combatting endogenic or exogenic depressions in mammals as quickly and expediently as possible. Moreover, they are also valuable intermediates in the preparation of other useful products, especially of pharmacologically active compounds.

Particularly useful are compounds of Formula I, wherein X represents two hydrogen atoms or oxo, R is hydrogen, lower alkyl, alkenyl, alkynyl, (3 to 7 ring-membered cycloalkyl, 5 to 7 ring-membered cycloalkenyl, Ph or Hc)-$C_mH_{2(m-q)}$, (PhCO, CN, carboxy or carbalkoxy)-$C_nH_{2n}$, (hydroxy, halogeno, amino, mono- or dialkylamino)-$C_pH_{2p}$ or halogeno-$C_pH_{2p-2}$, each of Ph and Ph' is phenyl, (lower alkyl)-phenyl, mono-, di- or tri-(lower alkoxy)-phenyl, (lower alkylmercapto, hydroxy, halogeno or trifluoromethyl)-phenyl, Hc is furyl, thienyl or pyridyl, unsubstituted or substituted by up to three methyl groups, $m$ is an integer from 0 to 4, $n$ such from 1 to 4, $p$ such from 2 to 4, $q$ such from 0 to 2 and ($m$-$q$) is positive; or an acyl derivative of the compounds wherein R is hydrogen or amino-$C_pH_{2p}$ and being derived from a lower alkane, di-lower alkylamino-lower alkane or 3 to 7 ring-membered cycloalkane or cycloalkyl-alkane monocarboxylic acid, the N-oxide of the compounds wherein R is lower alkyl, (cycloalkyl or Ph)-$C_mH_{2m}$ or (PhCO or carbalkoxy)-$C_nH_{2n}$, or a therapeutically acceptable acid addition salt thereof.

Preferred compounds of the invention are those of Formula I, wherein X represents two hydrogen atoms, R is lower alkyl, alkenyl, alkynyl, (3 to 5 ring-membered cycloalkyl, Ph, thienyl or furyl)-$C_mH_{2(m-q)}$, (PhCO, CN, carboxy or carbalkoxy)-$(CH_2)_n$, (hydroxy, halogeno, amino or dialkylamino)-$(CH_2)_p$ or halogeno-$C_pH_{2p-2}$, the multiple bonds in which radicals R are separated from the nitrogen atom by at least two carbon atoms, each of Ph and Ph' is phenyl, (lower alkyl)-phenyl, mono-, di- or tri-(lower alkoxy)-phenyl, (lower alkylmercapto, hydroxy, halogeno or trifluoromethyl)-phenyl, each of $m$ and $n$ is an integer from 1 to 3, $p$ such from 2 to 4, $q$ such from 0 to 2 and ($m$—$q$) is positive, or a therapeutically acceptable acid addition salt thereof.

Outstanding on account of their usefulness are the compounds of Formula II

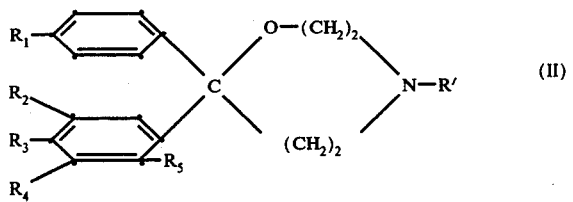

wherein R' is alkyl, alkenyl or alkynyl with up to 4 carbon atoms, the multiple bonds of which latter are separated from the nitrogen atom by at least two carbon atoms, (cyclopropyl, $R_1$-phenyl or furyl)-$C_mH_{2(m-q)}$—$CH_2$, ($R_1$-benzoyl, cyano, carboxy or carbethoxy)-$(CH_2)_n$ (hydroxy, fluoro, chloro, amino or dimethylamino)-$(CH_2)_p$ or chloro-$C_2H_2$—$CH_2$, $m$ is an integer from 0 to 2, $n$ such from 1 to 3, $p$ such from 2 to 3, $q$ such from 0 to 2 and ($m$—$q$) is positive, $R_1$ is hydrogen, methyl, methoxy, fluoro, chloro or trifluoromethyl, each of $R_2$ to $R_5$ is hydrogen, or one thereof is methyl, fluoro, chloro or trifluoromethyl, or up to three thereof are methoxy, and the others are hydrogen, or a therapeutically acceptable acid addition salt thereof.

The most preferred compounds are those of Formula II, wherein R' is allyl, propargyl, 2-butinyl, cyclopropylmethyl or 3-chloroallyl, each of $R_1$ and $R_2$ is hydrogen, methoxy or chloro, and each of $R_3$ to $R_5$ is hydrogen, or a therapeutically acceptable acid addition salt thereof.

The compounds of this invention are prepared according to conventional methods, for example by ring-closing compounds of Formulae III or IV

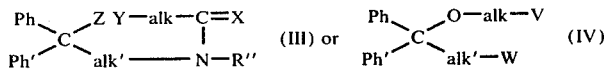

wherein one of Y and Z is hydroxy and the other is reactively esterified hydroxy, R'' is a group listed for R but different from hydrogen, one of V and W is CX'—NH—R'' and the other is reactively esterified HO—CX' or CHO, wherein X' is X, when present in V, or alk when present in W, hydrogenating any resulting Schiff's base obtained from IV and, if desired, converting any resulting compound of Formula I into another compound of the invention.

A reactively esterified hydroxy group Y, Z or derived from the alcohol containing HOCX', when X' = $H_2$, is preferably a halogen atom, advantageously chloro or bromo, or an aliphatic or aromatic sulfonyloxy group, such as alkane- or Ph-sulfonyloxy, e.g. mesyloxy, besyloxy, tosyloxy, closyloxy or brosyloxy; and such derived from the acid containing HOCX', when X' = O, is preferably said halogen atom, especially chloro.

Said ring-closure either occurs spontaneously at room temperature or below, as soon as V, W, Y and/or Z are formed from suitable precursors, e.g. amides, diols, acetals or acids respectively, or under pyroyltic conditions, for example at temperatures between room temperature and about 200° and/or in the presence of bases neutralizing the acids generated, such as alkali metal hydrides, hydroxides, carbonates or bicarbonates; or tert, amines, e.g. tri-lower alkylamines, pyridine or lower alkylated-pyridines.

The Schiff's bases obtained from compounds of Formula IV, with V or W being CHO, are hydrogenated in the customary manner, advantageously with the use of catalytically activated or nascent hydrogen, e.g. hydrogen in the presence of palladium or platinum caralysts, or generated electrolytically; or with the use of reducing agents, such as simple or complex light metal hydrides, such as borohydrides or alkali metal boro- or aluminum hydrides, e.g. sodium cyanoborohydride or lithium aluminum hydride.

In the compounds of Formula I so obtained, any oxo group X present therein may be reduced, for example with said complex hydrides, e.g. lithium aluminum hydride, or any α-aralkyl, e.g. benzyl group Ph—$C_mH_{2m}$ eliminated either reductively with said activated hydrogen, or by displacement with a reactive acylating agent, such as a halogenated carbonic acid ester, e.g. ethyl chloroformate, and resulting acyl derivatives hydrolyzed with aqueous solutions of suitably members of said bases, in order to obtain the compounds of Formula I with R=H. These, in turn, can be reacted with said reactive derivatives of the alcohols R—OH, or the acids mentioned for the acyl derivatives of said compounds of Formula I, under the conditions mentioned for said ring-closure, or corresponding olefines or oxiranes added, in order to obtain other compounds of Formula I with R being different from hydrogen or α-aralkyl respectively. Moreover, resulting compounds with unsaturated R can be hydrogenated with said activated hydrogen or cyano-$C_nH_{2n}$-compounds similarly reduced to $H_2N—C_{n+1}H_{2n+2}$ compounds respectively, and primary amines obtained mono- or di-alkylated with said reactive esters of lower alkanols or acylated with said reactive derivatives of said acids listed for the acyl derivatives of I. Any resulting amide or acyl derivative respectively, can be reduced with suitable members of said complex light metal hydrides, or reductively alkylated, in order to convert their carbonyl group into methylene.

Finally, resulting tert. amines sufficiently stable against oxidants, can be converted into N-oxides, for example, by treating them with suitable oxidation agents, such as hydrogen peroxide, aliphatic or aromatic percarboxylic acids, e.g. peracetic or perbenzoic acid. Any resulting base can be converted into a corresponding acid addition salt, preferably with the use of a terapeutically useful acid anion exchange preparation, or resulting salts can be converted into the corresponding free bases, for example, with the use of a base, such as a metal hydroxide, basic salt, ammonia, amino or cation exchange prepartion, e.g. an alkali metal hydroxide or carbonate. Said acid addition salts are preferably such of therapeutically acceptable inorganic or organic acids, such as strong metalloidic acids, for example hydrohalic, e.g. hydrochloric or hydrobromic acid; sulfuric, phosphoric, nitric or perchloric acid; aliphatic or aromatic carboxylic sulfonic acids, e.g. formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicylic, 4aminosalicylic, pamoic, nicotinic; methanesulfonic, ethanesulfonic, hydroxyethanesulfonic, ethylenesulfonic, halogen-benzenesulfonic, toluenesulfonic, naphthalenesulfonic, sulfanilic or cyclohexylsulfamic acid. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The starting material of Formula III can be prepared from the corresponding sec. amines or amides Ph, Ph′ CZ-alk′-NHR″ (described, together with their precursors, inter alia in J. Org. Chem. 33, 3402 (1968) or J. Chem. Soc. 1949, p.S144) by conventional acylation with said reactive derivatives of Y—$CH_2$—CX—OH, if desired by a following esterification of any diol obtained, e.g. with thionyl or phosphorus halides or oxyhalides or said sulfonic acids halides.

The compounds of Formula IV are similarly prepared, either from said sec. amines or amides with said derivatives of Y—$CH_2$—CX′—NH—R″, but choosing Y more reactive than the other functional group present in W, so that etherification occurs first, instead of N-substitution, as is the case for III. In order to prevent said N-substitution, the reactive esterification of HO-CX′ is performed after said etherification, or any aldehyde function liberated thereafter, for example from corresponding dialkyl or alkylene acetals. Any precursor-acid or -aldehyde Ph, Ph′CHO-alk-(CX′OH or CHO) is similarly prepared as the amines for III, i.e. from the preceding nitriles by hydrolysis or Stephen-reduction respectively (instead of hydrogenation in case of III).

In case mixtures of geometrical or optical isomers of the compounds of Formula I to IV are obtained, these can be separated into the single isomers by methods in themselves known, e.g. by fractional distillation, crystallization and/or chromatography. Racemic products can likewise be resolved into the optical antipodes, for example, by separation of diastereomeric salts thereof, e.g. by the fractional crystallization of d- or l-tartrates.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present process, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially valuable, e.g. those of Formula II.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweetners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods respectively and contain about 0.1 to 75%, preferably about 1 to 50%, of the active ingredient.

The following examples are intended to illustrate the invention and are not to be construed as being limitations thereon. Temperatures are given in degrees Centrigrade, and all parts wherever given are parts by weight. If not mentioned otherwise, all evaporations are performed under reduced pressure, preferably between about 15 and 100 mm Hg.

EXAMPLE 1

The solution of 19.3 g of N-benzyl-n-chloroacetyl-3-hydroxy-3,3-diphenylpropylamine in 150 ml of dimethylformamide is added dropwise to the suspension of 1.2 g of sodium hydride in 50 ml of dimethylformamide while stirring and cooling with an ice-bath. The mixture is allowed to warm up to room temperature, stirred for 15 hours and evaporated. The residue is partitioned between 150 ml methylene chloride and 50 ml of N hydrochloric acid, the organic layer separated, washed with water, dried, filtered and evaporated. The residue is triturated with diethyl ether and recrystallized from ethanol, to yield the 4-benzyl-3-oso-7,7-diphenyl-hexahydro-1,4-oxazepine of the formula

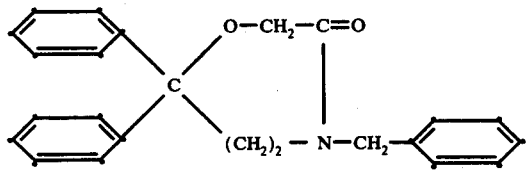

melting at 185° to 186°.

Analogously the following compounds of Formula I are prepared from equivalent amounts of the corresponding starting materials; X=O, R=benzyl

| No. | Ph | Ph' | m.p.° C |
|---|---|---|---|
| 1 | C$_6$H$_5$ | 2-CH$_3$O—C$_6$H$_4$ | 93–95 |
| 2 | '' | 3-CH$_3$O—C$_6$H$_4$ | 127–129 |
| 3 | '' | 3,4,5-(CH$_3$O)$_3$—C$_6$H$_2$ | 154–156 |
| 4 | '' | 3-Cl—C$_6$H$_4$ | 177–178 |
| 5 | 4-F—C$_6$H$_4$ | 4-F—C$_6$H$_4$ | 147–149 |

The starting material is prepared as follows:

The solution of 8.2 g of acetonitrile in 200 ml of tetrahydrofuran is added dropwise to the solution of 14.08 g of butyl lithium in 125 ml of tetrahydrofuran and 125 ml of n-hexane while stirring at −70° under nitrogen and stirring is continued for 1 hour. Thereupon the solution of 36.4 g benzophenone in 200 ml of tetrahydrofuran is added dropwise and the mixture stirred for 20 minutes at room temperature. It is poured onto 300 g of ice and 100 ml of 3N hydrochloric acid, the organic layer separated and the aqueous phase extracted three times with 50 ml of diethyl ether. The combined organic solutions are dried, evaporated and the residue recrystallized from ethanol, to yield the β-hydroxy-β,β-diphenyl-propionitrile melting at 136°–138°.

Analogously the nitriles corresponding to compounds No. 1 to 5 are prepared from equivalent amounts of the respective starting materials. They melt at 118°–120°, 75°–80°, 131°–133°, 86°–90° and 82°–87° respectively.

35.5 g of β-hydroxy-β,β-diphenyl-propionitrile are added portionwise to the stirred suspension of 12.9 g of lithium aluminum hydride in 800 ml of diethyl ether while cooling with an ice bath. After stirring for 15 hours at room temperature and 2 hours at the boil, it is cooled again and 12.9 ml of water, 12.9 ml of 15% aqueous sodium hydroxide and 38.7 ml of water are added in this order. The mixture is filtered, the residue washed 3 times with 150 ml of methylene chloride, the filtrate dried, evaporated and the residue recrystallized from ethanol, to yield the 3-hydroxy-3,3-diphenyl-propylamine melting at 134°–136°.

Analogously the amines corresponding to compounds No. 1 to 5 are prepared from equivalent amounts of the respective starting materials. They melt at 119°–122°, not above room temperature, 68°–72°, 72°–76° and 102°–107° respectively.

To the solution of 58.0 g of 3-hydroxy-3,3-diphenyl-propylamine in 700 ml of methylene chloride and 30.5 g of pyridine, that of 37.5 g of benzoyl chloride in 300 ml of methylene chloride is added dropwise during 2 hours while stirring and cooling with an ice-bath. Stirring is continued for 1 hour at 0°–5°, the mixture washed twice with 200 ml of N hydrochloric acid, 150 ml of 5% aqueous sodium hydroxide and 25 ml of water each, dried, evaporated and the residue triturated with diethyl ether, to yield the N-benzoyl-3-hydroxy-3,3-diphenylpropylamine melting at 140°–141°.

Analogously the amides corresponding to compounds No. 1,2,4 and 5 are prepared from equivalent amounts of the respective starting materials. They melt at 102°–104°, 132°–135°, 94°–96° and 144°–145° respectively.

72.3 g of N-benzoyl-3-hydroxy-3,3-diphenylpropylamine are added portionwise to the suspension of 16.3 g of lithium aluminum hydride in 1.6 lt of diethyl ether while stirring and cooling with an ice-bath. The mixture is stirred for 2 hours while warming to room temperature and 3 hours while refluxing. It is cooled again and 16.3 g of water, 16.3 ml of 15% aqueous sodium hydroxide and 49 ml water was added in this order, filtered and the residue washed 3 times with 300 ml of warm chloroform. The combined filtrates are dried and evaporated, to yield the N-benzyl-3-hydroxy-3,3-diphenylpropylamine melting at 145°–146°.

Analogously the amines corresponding to compounds No. 1,2,4 and 5 are prepared from equivalent amounts of the respective starting materials. They melt at 97°–100°, 60°–63°, 102°–104° and 97°–100° respectively.

These compounds can also be prepared as follows:

To the stirred mixture of 133.4 g of 3-hydroxy-3,3-diphenylpropylamine, 36 g of anhydrous magnesium sulfate and 250 ml of methylene chloride, the solution of 15.6 g of benzaldehyde in 50 ml of methylene chloride is added. The suspension is stirred for 15 hours at room temperature, heated to the boil and filtered. The residue is washed 3 times with 100 ml of methylene chloride, the combined filtrates evaporated and the residue recrystallized from ethanol, to yield the corresponding cyclic Schiff's base, i.e. the 2,6,6-triphenyl-tetrahydro-1,3-oxazine melting 163°–165°.

The mixture of 21.4 g thereof, 80 ml of anhydrous ethanol, containing 2.42 g of hydrogen chloride, and 3.0 g of 10% palladium on carbon is hydrogenated at room temperature and atmospheric pressure until the theoretical amount of hydrogen has been absorbed. It is filtered, the filtrate evaporated and the residue recrystallized from ethanol, to yield the N-benzyl-3-hydroxy-3,3-diphenylpropylamine melting at 146°–148°.

Analogously the N-benzyl-3-hydroxy-3-phenyl-3-(3,4,5-trimethoxyphenyl)-propylamine is prepared, melting at 108°–111°.

To the stirred solution of 15.6 g of N-benzyl-3-hydroxy-3,3-diphenylpropylamine in 7.0 g of di-isopropylethylamine and 150 ml of methylene chloride, that of 5.88 of chloroacetyl chloride in 50 ml of methylene chloride is added dropwise while stirring and cooling with an ice-bath. Thereupon the solution is stirred for 15 minutes at 0°–5° and washed successively with N hydrochloric acid, 10% aqueous sodium bicarbonate and finally with saturated aqueous sodium chloride. The organic layer is separated, dried, filtered and evaporated, to yield the N-benzyl-N-chloroacetyl-3-hydroxy-3,3-diphenylpropylamine showing in the I.R.-spectrum a strong band at 1640 cm$^{-1}$.

Analogously the starting materials corresponding to compounds No. 1 to 5 are prepared from equivalent amounts of the respective starting materials. Their main I.R.-bands are the following: 1644, 1645, 1650, 1650 and 1642 cm$^{-1}$ respectively.

EXAMPLE 2

17.8 g of 4-benzyl-3-oxo-7,7-diphenyl-hexahydro-1,4-oxazepine are added portionwise to the suspension of 2.28 g of lithium aluminum hydride in 300 ml of diethyl ether while stirring and cooling with an ice-bath. The mixture is allowed to warm up to room temperature and refluxed for 3½ hours. Then it is cooled with ice and 2.3 ml of water, 2.3 ml of 15% aqueous sodium hydroxide are added, followed by 6.9 ml of water. The suspension is filtered, the precipitate washed three times with 50 ml of hot methylene chloride, the combined filtrates dried, filtered and evaporated. The residue is taken up in acetone, the solution acidified with hydrogen chloride and diluted with diethyl ether, to yield the 4-benzyl-7,7-diphenyl-hexahydro-1,4-oxazepine hydrochloride melting at 243°–244° (the regenerated free base melts at 129°–131°.

Analogously the following free bases of Formula II are prepared from equivalent amounts of the corresponding starting materials: R'=benzyl

| No. | $R_1$ | $R_2$ | $R_3$ | $R_4$ | $R_5$ | m.p.° C |
|---|---|---|---|---|---|---|
| 1 | H | H | H | H | OCH$_3$ | 129–131 |
| 2 | H | OCH$_3$ | H | H | H | 78–80 |
| 3 | H | OCH$_3$ | OCH$_3$ | OCH$_3$ | H | 142–144 |
| 4 | H | Cl | H | H | H | 127–128 |
| 5 | F | H | F | H | H | 121–123 |

EXAMPLE 3

The mixture 42.5 g of 4-benzyl-7,7-diphenyl-hexahydro-1,4-oxazepine hydrochloride, 3.0 g of 10% of palladium on carbon and 750 ml of 95% aqueous ethanol is hydrogenated at 3 atmospheres and ambient temperature. After the theoretical amount of hydrogen has been absorbed, the mixture is filtered and the filtrate evaporated. The residue is partitioned between 200 ml of methylene chloride and 75 ml of 2N aqueous sodium hydroxide, the organic layer separated, washed with water, dried, filtered and evaporated. The residue is taken up in acetone and the solution acidified with cyclohexylsulfamic acid in acetone, to yield the 7,7-diphenyl-hexahydro-1,4-oxazepine cyclamate melting at 160°–162° (the regenerated free base melts at 72°–75°).

Analogously, the following compounds of Formula II are prepared from equivalent amounts of the corresponding starting materials: R' = H

| No. | $R_1$ | $R_2$ | $R_3$ | $R_4$ | $R_5$ | Salt | m.p.° C |
|---|---|---|---|---|---|---|---|
| 1 | H | H | H | H | OCH$_3$ | cyclamate | 111–113 |
| 2 | H | OCH$_3$ | H | H | H | cyclamate | 118–120 |
| 3 | H | OCH$_3$ | OCH$_3$ | OCH$_3$ | H | HCl | 193–195 |
| 4 | H | Cl | H | H | H | cyclamate | 138–140 |
| 5 | F | H | F | H | H | cyclamate | 161–162 |

Said compounds, especially 4, can also be prepared as follows:

To the solution of 30.25 g of 4-benzyl-7,7-diphenyl-hexahydro-1,4-oxazepine in 300 ml of methylene chloride, that of 10.4 g of ethyl chloroformate in 100 ml of methylene chloride is added dropwise while stirring. After 30 minutes the mixture is allowed to warm up to room temperature and stirred for 15 hours. It is successively washed twice with 50 ml of N hydrochloric acid, 50 ml of N aqueous sodium hydroxide and 50 ml of saturated sodium chloride each, dried, filtered and evaporated. The residue is recrystallized from hexane, to yield the 4-carbethoxy-7,7-diphenyl-hexahydro-1,4-oxazepine melting at 122° to 123°.

To the solution of 11.5 g thereof in 300 ml of ethanol, that of 30 g of potassium hydroxide in 70 ml of water is added and the mixture stirred and refluxed for 24 hours. It is evaporated, the residue taken up in 200 ml of water and the mixture extracted 3 times with 100 ml of diethyl ether. The combined organic solutions are re-extracted with N-hydrochloric acid, the aqueous solution made basic with sodium hydroxide and extracted with diethyl ether. The extract is washed with saturated aqueous sodium chloride, dried and evaporated, to yield the 7,7-diphenyl-hexahydro-1,4-oxazepine melting at 72°–75°.

EXAMPLE 4

To the stirred solution of 5.06 g of 7,7-diphenyl-hexahydro-1,4-oxazepine in 50 ml of methylene chloride, 2.6 g of allyl bromide are added, followed by 40 ml of 10% aqueous sodium bicarbonate and the mixture is stirred for 24 hours at room temperature. The organic layer is separated, washed with water, dried, filtered and evaporated. The residue is taken up in acetone, the solution acidified with hydrogen chloride in acetone and diluted with diethyl ether, to yield the 4-allyl-7,7-diphenyl-hexahydro-1,4-oxazepine hydrochloride melting at 246° to 247°.

Analogously the following compounds of Formula II are prepared from equivalent starting materials: $R_1$ = H

| No. | R' | $R_2$ | $R_3$ | $R_4$ | $R_5$ | Salt | m.p.° C |
|---|---|---|---|---|---|---|---|
| 1 | $CH_3$ | $OCH_3$ | $OCH_3$ | $OCH_3$ | H | HCl | 208–209 |
| 2 | allyl | " | " | " | H | " | 232–233 d. |
| 3 | " | " | H | H | H | " | 199–201 d. |
| 4 | " | Cl | H | H | H | " | 243–245 |
| 5 | " | F | H | F | H | " | 255–256 |
| 5a | " | H | H | H | $OCH_3$ | " | 240–242 d. |
| 6 | $(CH_3)_2C=CH-CH_2$ | H | H | H | H | " | 239–240 d. |

| No. | R' | $R_2$ | $R_3$ | $R_4$ | $R_5$ | Salt | m.p.° C |
|---|---|---|---|---|---|---|---|
| 7 | propargyl | H | H | H | H | " | 229–231 d. |
| 8 | " | $OCH_3$ | H | H | H | " | 187–189 |
| 9 | " | Cl | H | H | H | " | 218–220 |
| 10 | $CH_3-C\equiv C-CH_2$ | H | H | H | H | " | 217–219 |
| 11 | —$CH_2$ | H | H | H | H | " | 268–270 |
| 12 | 2-phenethyl | H | H | H | H | cyclamate | 159–161 |
| 13 | $C_6H_5-C\equiv C-CH_2$ | H | H | H | H | HCl | 105–110 |
| 14 | furfuryl | H | H | H | H | " | 240–242 d. |
| 15 | " | $OCH_3$ | H | H | H | " | 167–170 d. |
| 16 | $C_2H_5-CO-CH_2$ | H | H | H | H | " | 193–195 |
| 17 | $Cl-CH=CH-CH_2$ | H | H | H | H | " | 261–263 |
| 18 | " | $OCH_3$ | H | H | H | " | 174–177 d. |
| 19 | " | Cl | H | H | H | " | 223–225 d. |

EXAMPLE 5

The mixture of 3.20 g of 7,7-diphenyl-hexahydro-1,4-oxazepine, 2.54 g of 4-chloro-4'-fluoro-butyrophenone, 3.35 g of anhydrous potassium carbonate and 0.21 g of sodium iodide is refluxed for 22 hours, while stirring. The suspension is cooled, filtered, the filtrate evaporated and the residue dissolved in acetone. The solution is acidified with ethereal hydrogen chloride, to yield the 4-[3-(4-fluorobenzyl)-propyl]-7,7-diphenyl-hexahydro-1,4-oxazepine hydrochloride melting at 137°–140°.

Analogously the 4-(4'-chlorobenzoylmethyl)-7,7-diphenyl-hexahydro-1,4-oxazepine hydrochloride is prepared, melting at 102°–104°.

EXAMPLE 6

The mixture of 6.5 g of 7,7-diphenyl-hexahydro-1,4-oxazepine, 1.2 g of ethylene oxide, 0.5 ml of water and 20 ml of methanol is stirred at 40°–45° for 4 hours and at 50° for 2½ hours. It is cooled, the precipitate formed, filtered off and recrystallized from benzene-hexane, to yield the 4-(2-hydroxyethyl)-7,7-diphenyl-hexahydro-1,4-oxazepine melting at 122°–123° (its hydrochloride melts at 190°–192°).

EXAMPLE 7

The solution of 22.2 g of 7,7-diphenyl-hexahydro-1,4-oxazepine and 0.2 g of hydroquinone in 50 ml of acrylonitrile is refluxed for 18 hours, cooled and evaporated. The residue is taken up in chloroform, the mixture filtered through a short column of silica gel, eluted with chloroform and the eluate evaporated. The residue is recrystallized from ethanol, to yield the 4-(2-cyanoethyl)-7,7-diphenyl-hexahydro-1,4-oxazepine melting at 106°–107°.

EXAMPLE 8

3.06 g of 4-(2-cyanoethyl)-7,7-diphenyl-hexahydro-1,4-oxazepine are added portionwise to the suspension prepared by combining the solution of 1.33 g of anhydrous aluminum chloride in 30 ml of diethyl ether with that of 0.38 g of lithium aluminum hydride in 30 ml of diethyl ether while stirring and cooling with an ice-bath. The mixture is allowed to warm up to room temperature, stirred for 5½ hours and cooled again to 0°–5°. Thereupon 5 ml of water and 15 ml of 3N aqueous sulfuric acid are added and the organic layer extracted with 3N aqueous sulfuric acid. The aqueous layers are combined, made basic with concentrated aqueous sodium hydroxide and the mixture extracted four times with 15 ml of diethyl ether each. The extract is dried, filtered and evaporated. The residue is taken up in ethanol and the solution acidified with ethereal hydrogen chloride, to yield the 4-(3-aminopropyl)-7,7-diphenyl-hexahydro-1,4-oxazepine dihydrochloride melting at 190°–192° with decomposition.

EXAMPLE 9

To the solution of 6.2 g of 4-(3-aminopropyl)-7,7-diphenyl-hexahydro-1,4-oxazepine in 60 ml of acetonitrile, 8.4 ml of 37% aqueous formaldehyde are added while stirring and keeping the mixture at room temperature. Thereupon 2.0 g of sodium cyanoborohydride are added portionwise and after 15 minutes glacial acetic acid is added so that the pH of the solution is maintained at about 7. The solution is stirred for 45 minutes at said pH and evaporated. The residue is taken up in 80 ml of 2N aqueous potassium hydroxide, the mixture extracted three times with 50 ml of diethyl ether each, the extract washed with 0.5 N aqueous potassium hydroxide and re-extracted thrice with 40 ml of N hydrochloric acid each. The acidic extract is made basic with solid potassium hydroxide, extracted thrice with 50 ml of diethyl ether each, the extract dried, filtered and evaporated. The residue is taken up in ethanol and the solution acidified with ethereal hydrogen chloride, to yield the 4-(3-dimethylaminopropyl)-7,7-diphenyl-hexahydro-1,4-oxazepine dihydrochloride melting at 269°–271° with decomposition.

EXAMPLE 10

7.0 g of 4-carbethoxy-7,7-diphenyl-hexahydro-1,4-oxazepine (Example 3) are added portionwise to the suspension of 0.90 g of lithium aluminum hydride in 80 ml of diethyl ether while stirring and cooling with ice. The mixture is allowed to warm up to room temperature, refluxed for 6 hours and again cooled to 0° to 5°. Thereupon 0.9 ml of water, 0.9 ml of 15% aqueous sodium hydroxide and 2.7 ml of water are added in this order, the mixture is filtered, the filtrate dried and evaporated. The residue is taken up in acetone and the solution acidified with cyclohexylsulfamic acid in acetone, to yield the 4-methyl-7,7-diphenyl-hexahydro-1,4-oxazepine melting at 199° to 201°.

Analogously the 4-(cyclopropylmethyl, phenethyl and furfuryl)-7,7-diphenyl-hexahydro-1,4-oxazepine hydrochlorides are prepared from the corresponding amides prepared according to Example 11; they are identical with those obtained according to Example 4.

EXAMPLE 11

To the solution of 4.5 g of 7,7-diphenyl-hexahydro-1,4-oxazepine and 2.65 g of di-isopropyl-ethylamine in 30 ml of methylene chloride, that of 2.21 g of chloroactyl chloride in 25 ml of methylene chloride is added dropwise while stirring and cooling with ice. After stirring for 30 minutes at 0°–5°, the mixture is washed twice with 10 ml of cold N hydrochloric acid and 10 ml of cold 10% aqueous sodium carbonate each, dried, filtered and evaporated. The residue is triturated with diethyl ether and recrystallized from ethanol, to yield the 4-(2-chloroacetamido)-7,7-diphenyl-hexahydro-1,4-oxazepine melting at 150°–152°.

The solution of 5.0 g thereof in 20 ml of methylene chloride is added to that of 1.85 g of dimethylamine in 40 ml of methylene chloride and the mixture stirred for 5 hours at room temperature. It is washed with 2N aqueous sodium hydroxide, dried, filtered and evaporated. The residue is dissolved in acetone and the solution acidified with ethereal cyclohexylsulfamic acid, to yield the 4-(2-dimethylamino-acetamido)-7,7-diphenyl-hexahydro-1,4-oxazepine cyclamate melting at 183°–185°.

The analogously prepared 4-(cyclopropylcarbonyl and 2-furoyl)-7,7-diphenyl-hexahydro-1,4-oxazepines melt at 185°–187° and 261°–263° respectively.

EXAMPLE 12

To the solution of 2.5 g of 7,7-diphenyl-hexahydro-1,4-oxazepine in 5 ml of dimethylformamide, 1.5 g of anhydrous potassium carbonate are added while stirring, followed by the dropwise addition of the solution of 0.85 g of chloroacetonitrile in 2 ml of dimethylformamide and the suspension is stirred for 5 hours at room temperature. It is poured onto a mixture of ice and water, the aqueous phase extracted twice with 20 ml of diethyl ether each, the extract dried, filtered and evaporated. The residue is recrystallized from ethanol, to yield the 4-cyanomethyl-7,7-diphenyl-hexahydro-1,4-oxazepine melting at 119°–121° (its hydrochloride melts at 178°–180° with decomposition).

EXAMPLE 13

To the stirred solution of 5.0 g. of 4-(3-aminopropyl)-7,7-diphenyl-hexahydro-1,4-oxazepine and 2.0 g of triethylamine in 20 ml of methylene chloride, that of 3.2 g of adamantane-1-carboxylic acid chloride in 15 ml of methylene chloride is added while cooling to 0°. The mixture is stirred at said temperature for 15 minutes, washed with 2N aqueous sodium hydroxide, water, dried and evaporated. The residue dissolved in acetone, the solution acidified with cyclohexylsulfamic acid and the mixture diluted with diethyl ether, to yield the 4-[3-(1-adamantylcarboxamido)-propyl]-7,7-diphenyl-hexahydro-1,4-oxazepine cyclamate melting at 138°–140°.

EXAMPLE 14

Preparation of 10,000 tablets each containing 50.0 mg of the active ingredient:
Formula

| | |
|---|---|
| 4-allyl-7,7-diphenyl-hexahydro-1,4-oxazepine hydrochloride | 500.00 g |
| Lactose | 1,706.00 g |
| Corn starch | 90.00 g |
| Polyethylene glycol 6,000 | 90.00 g |
| Talcum powder | 90.00 g |
| Magnesium stearate | 24.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 45 ml of water and the suspension added to the boiling solution of the polyethylene glycol in 180 ml of water. The paste formed is added to the powders which are granulated, if necessary, with an additional amount of water. The granulate is dried overnight at 35°, broken on a screen with 1.2 mm openings and compressed into tablets using concave punches with 7.1 mm diameter, uppers bisected.

Preparation of 10,000 capsules each containing 100 mg of the active ingredient.
Formula

| | |
|---|---|
| 4-allyl-7,7-diphenyl-hexahydro-1,4-oxazepine hydrochloride | 1,000.0 g |
| Lactose | 2,800.0 g |
| Talcum powder | 200.0 g |

Procedure

All the powders are passed through a screen with openings of 0.6 mm. The drug substance is placed in a mixer and mixed first with the talcum, then with the lactose until homogeneous. No. 1 gelatin capsules are filled with 400 mg each, using a filling machine.

Analogously tablets or capsules of the other compounds of the invention are prepared, preferably of those corresponding to Formula II and being illustrated by the previous examples.

I claim:
1. A pharmaceutical composition comprising an antidepressively effective amount of a compound of the formula

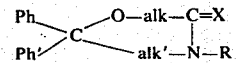

wherein X represents two hydrogen atoms or oxo, alk is methylidene, alk' is ethylene, R is hydrogen, lower alkyl, lower alkenyl, lower alkynyl, (lower cycloalkyl, lower cycloalkenyl or Ph -$C_mH_2$(m-q), (hydroxy, halogeno, amino, mono- or di-lower alkylamino)-$C_pH_{2p}$ or halogeno-$C_pH_{2p-2}$, each of Ph and Ph' is phenyl, unsubstituted or substituted by up to three members of lower alkyl, lower alkoxy, lower alkylmercapto, hydroxy, halogeno or trifluoromethyl, $m$ is an integer from 0 to 4, $p$ such from 2 to 4, $q$ such from 0 to 2 and $(m-q)$ is positive; or a therapeutically acceptable acid addition salt thereof, together with a pharmaceutical excipient.

2. The composition as claimed in claim 1, wherein the effective compound corresponds to the formula

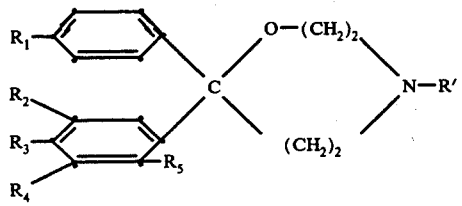

wherein R' is alkyl, alkenyl or alkynyl each with up to 4 carbon atoms, the multiple bonds of which latter are separated from the nitrogen atom by at least two carbon atoms, (cyclopropyl or $R_1$-phenyl)-$C_mH_{2(m-q)}$—$CH_2$, (hydroxy, fluoro, chloro, amino or dimethylamino)-$(CH_2)_p$ or chloro-$C_2H_2$—$CH_2$, $m$ is an integer from 0 to 2, $p$, such from 2 to 3, $q$ such from 0 to 2 and $(m-q)$ is positive, $R_1$ is hydrogen, methyl, methoxy, fluoro, chloro or trifluoromethyl, each of $R_2$ to $R_5$ is hydrogen, or one thereof is methyl, fluoro, chloro or trifluoromethyl, or up to three thereof are methoxy, and the others are hydrogen, or a therapeutically acceptable acid addition salt thereof.

3. The composition as claimed in claim 2, in which formula of the effective compound R' is allyl, 2-butinyl, cyclopropylmethyl or 3-chloroallyl, each of $R_1$ and $R_2$ is hydrogen, methoxy or chloro, and each of $R_3$ to $R_5$ is hydrogen, or a therapeutically acceptable acid addition salt thereof.

4. The composition as claimed in claim 2, wherein the effective compound is the 4-allyl-7,7-diphenyl-hexahydro-1,4-oxazepine or a therapeutically acceptable acid addition salt thereof.

* * * * *